US008524664B2

(12) United States Patent (10) Patent No.: US 8,524,664 B2
Dores (45) Date of Patent: Sep. 3, 2013

(54) METHODS OF TREATING OVERPRODUCTION OF CORTISOL USING ACTH ANTAGONIST PEPTIDES

(75) Inventor: Robert M. Dores, Littleton, CO (US)

(73) Assignee: Colorado Seminary, Which owns and Operates The Univeristy of Denver, Denver, CO (US)

( * ) Notice: Subject to any disclaimer, the term of this patent is extended or adjusted under 35 U.S.C. 154(b) by 0 days.

(21) Appl. No.: 13/152,233

(22) Filed: Jun. 2, 2011

(65) Prior Publication Data

US 2012/0309696 A1 Dec. 6, 2012

(51) Int. Cl.
*A61K 38/08* (2006.01)
*A61K 38/35* (2006.01)
(52) U.S. Cl.
USPC ........................................ 514/10.8; 514/21.6
(58) Field of Classification Search
None
See application file for complete search history.

(56) References Cited

U.S. PATENT DOCUMENTS

| | | | |
|---|---|---|---|
| 5,296,483 A | 3/1994 | Bodor | |
| 5,312,817 A | 5/1994 | Snorrason | |
| 5,445,829 A | 8/1995 | Paradissis et al. | |
| 5,472,704 A | 12/1995 | Santus et al. | |
| 5,672,356 A | 9/1997 | Rault et al. | |
| 6,080,736 A | 6/2000 | Landry et al. | |
| 6,150,354 A | 11/2000 | Davis et al. | |
| 6,319,919 B1 | 11/2001 | Davis et al. | |
| 6,403,597 B1 | 6/2002 | Wilson et al. | |
| 6,482,440 B2 | 11/2002 | Zemlan et al. | |
| 6,524,621 B2 | 2/2003 | Adjei et al. | |
| 6,528,080 B2 | 3/2003 | Dunn et al. | |
| 6,537,579 B1 | 3/2003 | Desai et al. | |
| 6,541,020 B1 | 4/2003 | Ding et al. | |
| 6,548,084 B2 | 4/2003 | Leonard et al. | |
| 6,562,375 B1 | 5/2003 | Sako et al. | |
| 6,565,883 B2 | 5/2003 | Ogorka et al. | |
| 6,569,463 B2 | 5/2003 | Patel et al. | |
| 6,589,563 B2 | 7/2003 | Prokop | |
| 6,596,308 B2 | 7/2003 | Gutierrez-Rocca et al. | |
| 6,599,529 B1 | 7/2003 | Skinhoj et al. | |
| 6,607,751 B1 | 8/2003 | Odidi et al. | |
| 6,613,358 B2 | 9/2003 | Randolph et al. | |
| 6,613,361 B1 | 9/2003 | Lebon et al. | |
| 6,624,200 B2 | 9/2003 | Bologna et al. | |
| 6,635,680 B2 | 10/2003 | Mulye | |
| 6,638,521 B2 | 10/2003 | Dobrozsi | |
| 7,264,314 B2 | 9/2007 | Brennan et al. | |

FOREIGN PATENT DOCUMENTS

WO 2006/052468 A2 5/2006

OTHER PUBLICATIONS

Schrama et al. J. Neurochemistry 43(6): 1693-1698, 1984.*
Seelig et al. FEBS Letters 19(3): 232-234, 1971.*
Bao, J., "Capillary electrophoretic immunoassays" Journal of Chromatography B: Biomedical Sciences and Applications, 1997, vol. 699, Iss. 1-2, pp. 463-480.
Cone, R., "Studies on the Physiological Functions of the Melanocortin System," Endocrine Reviews, 2006, vol. 27, No. 7, pp. 736-749.
Fink, P.C., et al., "Measurement of Proteins with the Behring Nephelometer—A Multicentre Evaluation," Journal of Clinical Chemistry and Clinical Biochemistry, 1989, vol. 27, pp. 261-276.
Hinkle, P., et al., "Structure and function of the melanocortin2 receptor accessory protein (MRAP)," Molecular and Cellular Endocrinology, 2009, vol. 300, Iss. 1-2, pp. 25-31.
Huang, Y., et al., "Effects of Manufacturing Process Variables on In Vitro Dissolution Characteristics of Extended-Release Tablets Formulated with Hydroxypropyl Methylcellulose," Drug Development and Industrial Pharmacy, 2003, vol. 29, No. 1, pp. 79-88.
Khanvilkar, K., et al., "Influence of Hydroxypropyl Methylcellulose Mixture, Apparent Viscosity, and Tablet Hardness on Drug Release Using a $2^3$ Full Factorial Design," Drug Development and Industrial Pharmacy, 2002, vol. 28, No. 5, pp. 601-608.
Maggi, L., et al., "Photostability of extended-release matrix formulations," European Journal of Pharmaceutics and Biopharmaceutics, 2003, vol. 55, Iss. 1, pp. 99-105.
Merrifield, R. B., Solid Phase Peptide Synthesis. I. The Synthesis of a Tetrapeptide, Journal of the American Chemical Society, 1963, vol. 85, Iss. 14, pp. 2149-2154.
Pearnchob, N., et al., "Pharmaceutical Applications of Shellac: Moisture-Protective and Taste-Masking Coatings and Extended-Release Matrix Tablets," Drug Development and Industrial Pharmacy, 2003, vol. 29, No. 8, pp. 925-938.
Rongen, H., et al., "Liposomes and immunoassays," Journal of Immunological Methods, 1997, vol. 204, Iss. 2, pp. 105-133.
Schmalzing, D., et al., "Capillary electrophoresis based immunoassays: A critical review" Electrophoresis, 1997, vol. 18, Iss. 12-13, pp. 2184-2193.
Schmidt, C, et al., "A multiparticulate drug-delivery system based on pellets incorporated into congealable polyethylene glycol carrier materials," International Journal of Pharmaceutics, 2001, vol. 216, Iss. 1-2, pp. 9-16.
Schwyzer,R., "ACTH: A Short Introductory Review," Annals of the New York Academy of Sciences, 1977, vol. 297, pp. 3-26.
Seelig, S., et al., "A new approach to the structure-activity relationship for ACTH analogs using isolated adrenal cortex cells" Methods in Enzymology, 1975, vol. 39, pp. 347-359.
Yang,Y., et al., "Structural insights into the role of the ACTH receptor cysteine residues on receptor function," American Journal of Physiology—Regulatory, Integrative and Comparative Physiology, 2007, vol. 293, Iss. 3, R1120-R1126.
Veo, Kristopher et al., "Observations on the ligand selectivity of the melanocortin 2 receptor," General and Comparative Endocrinology, 2011, pp. 3-9, Elsevier, Inc.

* cited by examiner

*Primary Examiner* — Christine J Saoud
(74) *Attorney, Agent, or Firm* — Kilpatrick Townsend & Stockton LLP

(57) ABSTRACT

The present invention provides methods of treating overproduction of cortisol in a subject by administering to the subject a peptide that antagonizes adrenocorticotropin hormone (ACTH) to block the activation of melanocortin 2 receptors.

22 Claims, 4 Drawing Sheets

SEQUENCE LISTING

```
<160> NUMBER OF SEQ ID NOS: 19

<210> SEQ ID NO 1
<211> LENGTH: 10
<212> TYPE: PRT
<213> ORGANISM: Artificial Sequence
<220> FEATURE:
<223> OTHER INFORMATION: synthetic adrenocorticotropin hormone analog
      ACTH(15-24) peptide, human ACTH residues 15-24,
      ACTH antagonist polypeptide

<400> SEQUENCE: 1

Lys Lys Arg Arg Pro Val Lys Val Tyr Pro
 1               5                   10

<210> SEQ ID NO 2
<211> LENGTH: 11
<212> TYPE: PRT
<213> ORGANISM: Artificial Sequence
```

```
<220> FEATURE:
<223> OTHER INFORMATION: synthetic adrenocorticotropin hormone analog
      ACTH(15-25) peptide, human ACTH residues 15-25,
      ACTH antagonist polypeptide

<400> SEQUENCE: 2

Lys Lys Arg Arg Pro Val Lys Val Tyr Pro Asn
1               5                   10

<210> SEQ ID NO 3
<211> LENGTH: 39
<212> TYPE: PRT
<213> ORGANISM: Homo sapiens
<220> FEATURE:
<223> OTHER INFORMATION: human full-length adrenocorticotropin hormone
      (ACTH)

<400> SEQUENCE: 3

Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
        35

<210> SEQ ID NO 4
<211> LENGTH: 24
<212> TYPE: PRT
<213> ORGANISM: Artificial Sequence
<220> FEATURE:
<223> OTHER INFORMATION: synthetic truncated adrenocorticotropin hormone
      analog ACTH(1-24) peptide, human ACTH residues 1-24

<400> SEQUENCE: 4

Ser Tyr Ser Met Glu His Phe Arg Trp Gly Lys Pro Val Gly Lys Lys
1               5                   10                  15

Arg Arg Pro Val Lys Val Tyr Pro
            20

<210> SEQ ID NO 5
<211> LENGTH: 5
<212> TYPE: PRT
<213> ORGANISM: Artificial Sequence
<220> FEATURE:
<223> OTHER INFORMATION: synthetic adrenocorticotropin hormone
      polypeptide fragment, human ACTH motif, ACTH residues 15-19,
      secondary site involved with melanocortin 2 receptor (MC2R)
      activation

<400> SEQUENCE: 5

Lys Lys Arg Arg Pro
1               5

<210> SEQ ID NO 6
<211> LENGTH: 8
<212> TYPE: PRT
<213> ORGANISM: Artificial Sequence
<220> FEATURE:
<223> OTHER INFORMATION: synthetic adrenocorticotropin hormone analog
      ACTH(17-24) peptide, human ACTH residues 17-24

<400> SEQUENCE: 6

Arg Arg Pro Val Lys Val Tyr Pro
1               5

<210> SEQ ID NO 7
<211> LENGTH: 14
```

```
<212> TYPE: PRT
<213> ORGANISM: Artificial Sequence
<220> FEATURE:
<223> OTHER INFORMATION: synthetic adrenocorticotropin hormone analog
      ACTH(11-24) peptide, human ACTH residues 11-24

<400> SEQUENCE: 7

Lys Pro Val Gly Lys Lys Arg Arg Pro Val Lys Val Tyr Pro
 1               5                  10

<210> SEQ ID NO 8
<211> LENGTH: 4
<212> TYPE: PRT
<213> ORGANISM: Artificial Sequence
<220> FEATURE:
<223> OTHER INFORMATION: synthetic adrenocorticotropin hormone (ACTH) or
      melanocortin N-terminal motif

<400> SEQUENCE: 8

His Phe Arg Trp
 1

<210> SEQ ID NO 9
<211> LENGTH: 13
<212> TYPE: PRT
<213> ORGANISM: Homo sapiens
<220> FEATURE:
<223> OTHER INFORMATION: human alpha melanocyte-stimulating hormone
      (alpha-MSH), melanotropin alpha
<220> FEATURE:
<221> NAME/KEY: MOD_RES
<222> LOCATION: (1)...(1)
<223> OTHER INFORMATION: N-acetyl-serine (NAc-S)
<220> FEATURE:
<221> NAME/KEY: MOD_RES
<222> LOCATION: (13)...(13)
<223> OTHER INFORMATION: valinamide

<400> SEQUENCE: 9

Ser Tyr Ser Met Glu His Phe Arg Trp Gly Lys Pro Val
 1               5                  10

<210> SEQ ID NO 10
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 10

Ser Tyr Ser Met Glu Ala Ala Ala Ala Gly Lys Pro Val Gly Lys Lys
 1               5                  10                  15

Arg Arg Pro Val Lys Val Tyr Pro
             20

<210> SEQ ID NO 11
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 11

Ser Tyr Ser Met Glu His Phe Ala Trp Gly Lys Pro Val Gly Lys Lys
 1               5                  10                  15

Arg Arg Pro Val Lys Val Tyr Pro
             20
```

```
<210> SEQ ID NO 12
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 12

Ser Tyr Ser Met Glu His Ala Arg Trp Gly Lys Pro Val Gly Lys Lys
1               5                  10                  15

Arg Arg Pro Val Lys Val Tyr Pro
            20

<210> SEQ ID NO 13
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 13

Ser Tyr Ser Met Glu His Phe Arg Trp Gly Lys Pro Val Gly Ala Ala
1               5                  10                  15

Ala Ala Ala Val Lys Val Tyr Pro
            20

<210> SEQ ID NO 14
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 14

Ser Tyr Ser Met Glu His Phe Arg Trp Gly Lys Pro Val Gly Ala Ala
1               5                  10                  15

Arg Arg Pro Val Lys Val Tyr Pro
            20

<210> SEQ ID NO 15
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 15

Ser Tyr Ser Met Glu His Phe Arg Trp Gly Lys Pro Val Gly Lys Lys
1               5                  10                  15

Ala Ala Ala Val Lys Val Tyr Pro
            20

<210> SEQ ID NO 16
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 16
```

-continued

```
Ser Tyr Ser Met Glu His Phe Arg Trp Ala Ala Ala Ala Lys Lys
 1               5                  10                  15

Arg Arg Pro Val Lys Val Tyr Pro
            20

<210> SEQ ID NO 17
<211> LENGTH: 9
<212> TYPE: PRT
<213> ORGANISM: Artificial Sequence
<220> FEATURE:
<223> OTHER INFORMATION: synthetic adrenocorticotropin hormone (ACTH)
      analog

<400> SEQUENCE: 17

Lys Lys Arg Arg Pro Ala Ala Ala Ala
 1               5

<210> SEQ ID NO 18
<211> LENGTH: 5
<212> TYPE: PRT
<213> ORGANISM: Artificial Sequence
<220> FEATURE:
<223> OTHER INFORMATION: synthetic adrenocorticotropin hormone (ACTH)
      region

<400> SEQUENCE: 18

Val Lys Val Tyr Pro
 1               5

<210> SEQ ID NO 19
<211> LENGTH: 24
<212> TYPE: PRT
<213> ORGANISM: Artificial Sequence
<220> FEATURE:
<223> OTHER INFORMATION: synthetic adrenocorticotropin hormone (ACTH)
      analog AT814 with modified KKRRP motif

<400> SEQUENCE: 19

Ser Tyr Ser Met Glu His Phe Arg Trp Gly Lys Pro Val Gly Lys Arg
 1               5                  10                  15

Ala Ala Trp Val Lys Val Tyr Pro
            20
```

METHODS OF TREATING OVERPRODUCTION OF CORTISOL USING ACTH ANTAGONIST PEPTIDES

STATEMENT AS TO RIGHTS TO INVENTIONS MADE UNDER FEDERALLY SPONSORED RESEARCH OR DEVELOPMENT

This invention was made with Government support under National Science Foundation Grant Number IOB-0516958. The Government has certain rights in the invention.

BACKGROUND OF THE INVENTION

Adrenocorticotropin, or ACTH, is a hormone that is secreted by the pituitary gland in response to physiological or psychological stress. In response to a signal from corticotrophin-releasing hormone (CRH) that is released in the hypothalamus under stress, ACTH is produced by cleavage of a large precursor molecule, pro-opiomelanocortin (POMC). Secreted. ACTH, then travels to the adrenal cortex, where it binds to and activates melanocortin 2 receptors (MC2Rs) located primarily on the cell surface of adrenocortical cells of the adrenal glands. Activation of MC2R in turn leads to the production of the internal second messenger, cAMP, in the adrenal cell. cAMP binds and activates protein kinase (PKA), which activates enzymes leading to the conversion of the lipid cholesterol to the steroid hormone cortisol.

Cortisol is a vital hormone that affects numerous biological processes in order to restore homeostasis after stress. Some processes regulated by cortisol include regulating glucose homeostasis, increasing blood pressure, gluconeogenesis, promoting metabolism of glycogen, lipids, and proteins, and suppressing the immune system. Under normal physiological conditions, cortisol levels are tightly coordinated. However, in some conditions such as Cushing's Syndrome and chronic stress, cortisol is overproduced. The overproduction of cortisol has been shown to have many negative effects, such as damaging the hippocampus, a region of the brain that is critical for cognitive functions and regulation of the hypothalamus/pituitary/adrenal axis; increasing fat deposits, blood pressure levels, and blood sugar levels; bone loss; muscle weakness; and weakening (suppression) of the immune system.

Accordingly, there is a need for methods of preventing or decreasing ACTH-dependent overproduction of cortisol. The present invention satisfies this need and others.

BRIEF SUMMARY OF THE INVENTION

The present invention provides ACTH antagonist polypeptides that inhibit ACTH-dependent activation of MC2R. Because ACTH-dependent activation of MC2R induces the production and secretion of cortisol, the ACTH antagonist polypeptides of the present invention are useful, for example, in treating diseases and conditions characterized by the overproduction of cortisol.

In one aspect, the present invention provides methods of treating a subject having a condition characterized by the overproduction of cortisol. In some embodiments, the method comprises administering to the subject an agent that significantly inhibits activation of a melanocortin 2 receptor (MC2R) without significantly inhibiting activation of a melanocortin receptor other than MC2R (i.e., MC1R, MC3R, MC4R, or MC5R).

In some embodiments, the agent is a polypeptide having the amino acid sequence of KKRRPVKVYP (SEQ ID NO:1) or KKRRPVKVYPN (SEQ ID NO:2). In some embodiments, the agent is a polypeptide having the amino acid sequence of KKRRPVKVYP (SEQ ID NO:1). In some embodiments, the agent is a polypeptide having the amino acid sequence of KKRRPVKVYPN (SEQ ID NO:2).

In some embodiments, the agent reduces adrenocorticotropin hormone (ACTH)-induced production of cortisol by at least 10%.

In some embodiments, the subject is human. In some embodiments, the subject has a condition selected from the group consisting of Cushing's syndrome, tumor of the anterior pituitary, chronic stress, and trauma.

In some embodiments, the agent is administered systemically. In some embodiments, the agent is administered by intravenous injection. In some embodiments, the agent is administered in a sustained release formulation. In some embodiments, the agent is administered in a therapeutically effective dose. In some embodiments, the agent is co-administered with one or more additional therapeutic agents.

In another aspect, the present invention provides methods of treating overproduction of cortisol in a population of non-human animals. In some embodiments, the method comprises administering to the non-human animals an agent that significantly inhibits activation of a melanocortin 2 receptor (MC2R) without significantly inhibiting activation of a melanocortin receptor other than MC2R.

In some embodiments, the non-human animals produce cortisol at a level that is associated with chronic stress in the non-human animals. In some embodiments, the non-human animals are fish. In some embodiments, the non-human animals are chickens.

In some embodiments, the agent is a polypeptide having the amino acid sequence of KKRRPVKVYP (SEQ ID NO:1) or KKRRPVKVYPN (SEQ ID NO:2). In some embodiments, the agent is a polypeptide having the amino acid sequence of KKRRPVKVYP (SEQ ID NO:1). In some embodiments, the agent is a polypeptide having the amino acid sequence of KKRRPVKVYPN (SEQ ID NO:2).

In some embodiments, the agent reduces adrenocorticotropin hormone (ACTH)-induced production of cortisol by at least 10%.

In some embodiments, the agent is administered systemically. In some embodiments, the agent is administered in a sustained release formulation.

In yet another aspect, the present invention provides a method of inhibiting adrenocorticotropin hormone (ACTH)-dependent activation of a melanocortin 2 receptor (MC2R). In some embodiments, the method comprises contacting a cell expressing ACTH with a polypeptide having the amino acid sequence of KKRRPVKVYP (SEQ ID NO:1) or KKRRPVKVYPN (SEQ ID NO:2); thereby inhibiting ACTH-dependent activation of the MC2R.

In some embodiments, the cell is contacted with the polypeptide at a concentration sufficient to inhibit ACTH-dependent, activation of the MC2R by at least about 10%, at least about 20%, at least about 30%, at least about 40%, at least about 50%, at least about 60%, at least about 70%, at least about 80%, or at least about 90%.

In some embodiments, the agent is a polypeptide having the amino acid sequence of KKRRPVKVYP (SEQ ID NO:1). In some embodiments, the agent is a polypeptide having the amino acid sequence of KKRRPVKVYPN (SEQ ID NO:2).

In still another aspect, the present invention provides compositions comprising a polypeptide having the amino acid sequence of KKRRPVKVYP (SEQ ID NO:1) or KKRRPVKVYPN (SEQ ID NO:2). In some embodiments, the composition comprises a polypeptide having the amino acid sequence of KKRRPVKVYP (SEQ ID NO:1). In some embodiments, the composition comprises a polypeptide having the amino acid sequence of KKRRPVKVYPN (SEQ ID NO:2). In some embodiments, the composition further comprises a pharmaceutically acceptable excipient. In some embodiments, the composition further comprises one or more additional therapeutic agents.

In yet another aspect, the present invention provides kits for treating a subject having a condition characterized by overproduction of cortisol. In some embodiments, the kit comprises a polypeptide having the amino acid sequence of KKRRPVKVYP (SEQ ID NO:1) or KKRRPVKVYPN (SEQ ID NO:2). In some embodiments, the kit comprises a polypeptide having the amino acid sequence of KKRRPVKVYP (SEQ ID NO:1). In some embodiments, the kit comprises a polypeptide having the amino acid sequence of KKRRPVKVYPN (SEQ ID NO:2). In some embodiments, the kit comprises a polypeptide having the amino acid sequence of KKRRPVKVYP (SEQ ID NO:1) or KKRRPVKVYPN (SEQ ID NO:2) formulated with a pharmaceutically acceptable excipient. In some embodiments, the kit further comprises one or more additional therapeutic agents.

Definitions

"Adrenocorticotropin hormone" or "ACTH" refers to a peptide hormone produced and secreted by the anterior pituitary gland that stimulates the adrenal cortex to secrete glucocorticoids such as cortisol. In some embodiments, ACTH includes a human full-length. ACTH polypeptide having the amino acid sequence SYSMEHFRWGKPVGKKRRPVKVYPNGAEDESAEAFPLEF (SEQ ID NO:3) or a truncated human ACTH polypeptide that retains the activity of full-length ATCH, e.g., a polypeptide having the amino acid sequence SYSMEHFRWGKPVGKKRRPVKVYP (SEQ ID NO:4) (ACTH(1-24)).

"Cortisol" refers to a glucocorticoid, or steroid hormone, that is produced and secreted by the adrenal gland in response to stress and which functions to increase blood sugar, suppress the immune system, and aid in fat, protein, and carbohydrate metabolism.

"Melanocortin receptor" refers to a member of a family of G protein-coupled receptors which are activated by one or more melanocortins derived from pro-opiomelanocortin, including ACTH. There are five known melanocortin receptors, melanocortin 1 receptor (MC1R), melanocortin 2 receptor (MC2R), melanocortin 3 receptor (MC3R), melanocortin 4 receptor (MC4R), and melanocortin 5 receptor (MC5R).

As used herein, the term "condition characterized by overproduction of cortisol" refers to a disease or condition in which the adrenal gland (or an equivalent structure, e.g., the head kidney in fish) produces and/or secretes a amount of cortisol that is significantly higher relative to a normal (i.e., non-diseased) organism. In some embodiments, the amount of cortisol that is produced by a subject having a condition characterized by overproduction of cortisol is at least 10%, 20%, 30%, 40%, 50%, 60%, 70%, 80%, 90%, 100%, 150%, 200%, or greater as compared the amount of cortisol that is produced by a control non-diseased subject. In some embodiments, the condition is Cushing's Syndrome, chronic stress, trauma, or a tumor of the anterior pituitary.

As used herein, an "agent" refers to any molecule, either naturally occurring or synthetic, e.g., protein, oligopeptide (e.g., from about 5 to about 25 amino acids in length, e.g., about 5, 6, 7, 8, 9, 10, 11, 12, 13, 14, 15, 16, 17, 18, 19, 20, 21, 22, 23, 24, or 25 amino acids in length), small organic molecule, polysaccharide, lipid, fatty acid, polynucleotide, RNAi, siRNA, antibody, oligonucleotide, etc., that has or may have a pharmacological activity. Agents include molecules that are known drugs, molecules for which pharmacological activity has been identified but which are undergoing further therapeutic evaluation, and molecules that are members of collections and libraries that are to be screened for a pharmacological activity. In some embodiments, the agent is a polypeptide fragment comprising the KKRRP (SEQ ID NO:5) motif in ACTH. In some embodiments, the agent is a polypeptide having the amino acid sequence KKRRPVKVYP (SEQ ID NO:1) or KKRRPVKVYPN (SEQ ID NO:2).

The term "peptide," "polypeptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally-occurring α-amino acids and their stereoisomers, as well as unnatural amino acids and their stereoisomers. "Stereoisomers" of amino acids includes mirror image isomers of the amino acids, such as L-amino acids or D-amino acids. The naturally occurring amino acids are L-amino acids. Naturally occurring amino acids are those encoded by the genetic code, as well as those amino acids that are later modified, e.g., hydroxyproline, γ-carboxyglutamate, and O-phosphoserine. "Unnatural amino acids" include, but are not limited to, amino acid analogs, amino acid mimetics, and synthetic amino acids. Unnatural amino acids are not encoded by the genetic code and can, but do not necessarily have the same basic structure as a naturally occurring amino acid. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

The terms "inhibiting," "reducing," and "decreasing," with respect to activation of a melanocortin receptor or production of cortisol, refers to inhibiting the activation of signaling molecules downstream of a melanocortin receptor or inhibiting the production or secretion of cortisol from the adrenal gland, respectively, by a measurable amount using any method known in the art. The activation of a melanocortin receptor is inhibited, reduced, or decreased if the level of a downstream signaling molecule (e.g., cAMP) is at least about 10%, 20%, 30%, 40%, 50%, 60%, 70%, 80%, 90% or more reduced subsequent to administration of an agent as described herein (e.g., a polypeptide having the amino acid sequence of SEQ ID NO:1 or SEQ ID NO:2) as compared to the level of the downstream signaling molecule prior to administration of the agent. The production of cortisol is inhibited, reduced, or decreased if the amount of cortisol that is secreted subsequent to administration of an agent as described herein (e.g., a polypeptide having the amino acid sequence of SEQ ID NO:1 or SEQ ID NO:2) is at least about 10%, 20%, 30%, 40%, 50%, 60%, 70%, 80%, 90% or more reduced as compared to the amount of cortisol that is secreted prior to administration of the agent. As used herein, the term "significantly inhibits" refers to an inhibition, reduction, or decrease of at least 10%.

The term "sample" or "biological sample" blood and blood fractions or products (e.g., serum, plasma, platelets, red blood cells, and the like), sputum, tissue, cultured cells, e.g., primary cultures, explants, and transformed cells, stool, urine, etc., obtained from a subject. A "subject" refers to a eukaryotic organism, e.g., a mammal (for example, a human or a non-human primate (e.g., chimpanzee, macaque, orangutan); a domesticated mammal (e.g., feline, canine); an agricultural mammal (e.g., bovine, equine, porcine, ovine); or a laboratory mammal (e.g., lagomorpha, rattus, murine, hamster)); or a bird (e.g., chicken, turkey, duck, or goose); reptile; or fish (e.g., salmon).

As used herein, the terms "treating" and "treatment" refer to delaying the onset of, retarding or reversing the progress of, or alleviating or preventing either the disease or condition to which the term applies, or one or more symptoms of such disease or condition.

The term "therapeutically effective amount or dose" refers to a dose of an agent (e.g., a polypeptide having the, amino acid sequence of SEQ ID NO:1 or SEQ ID NO:2) that is capable of achieving a therapeutic effect in a subject in need thereof. For example, a therapeutically effective amount of a polypeptide having the amino acid sequence of SEQ ID NO:1 or SEQ ID NO:2 can be the amount that is capable of preventing or relieving one or more symptoms of a condition characterized by the overproduction of cortisol (e.g., Cushing's Syndrome). The exact amount can be ascertainable by one skilled in the art using known techniques (see, e.g., Lieberman, *Pharmaceutical Dosage Forms*, Vols. 1-3 (1992); Lloyd, *The Art, Science and Technology of Pharmaceutical Compounding* (1999); Pickar, *Dosage Calculations* (1999); and *Remington: The Science and Practice of Pharmacy*, 20th Edition, Gennaro, Ed., Lippincott, Williams & Wilkins (2003)).

The terms "sustained release" and "extended release" are used in their conventional sense to refer to a formulation of a therapeutic agent that provides for gradual release of the therapeutic agent over an extended period of time, for example, 12 hours or more, and that preferably, although not necessarily, results in substantially steady-state blood levels of the therapeutic agent over an extended time period.

DETAILED DESCRIPTION OF THE INVENTION

I. Introduction

Figure 1:
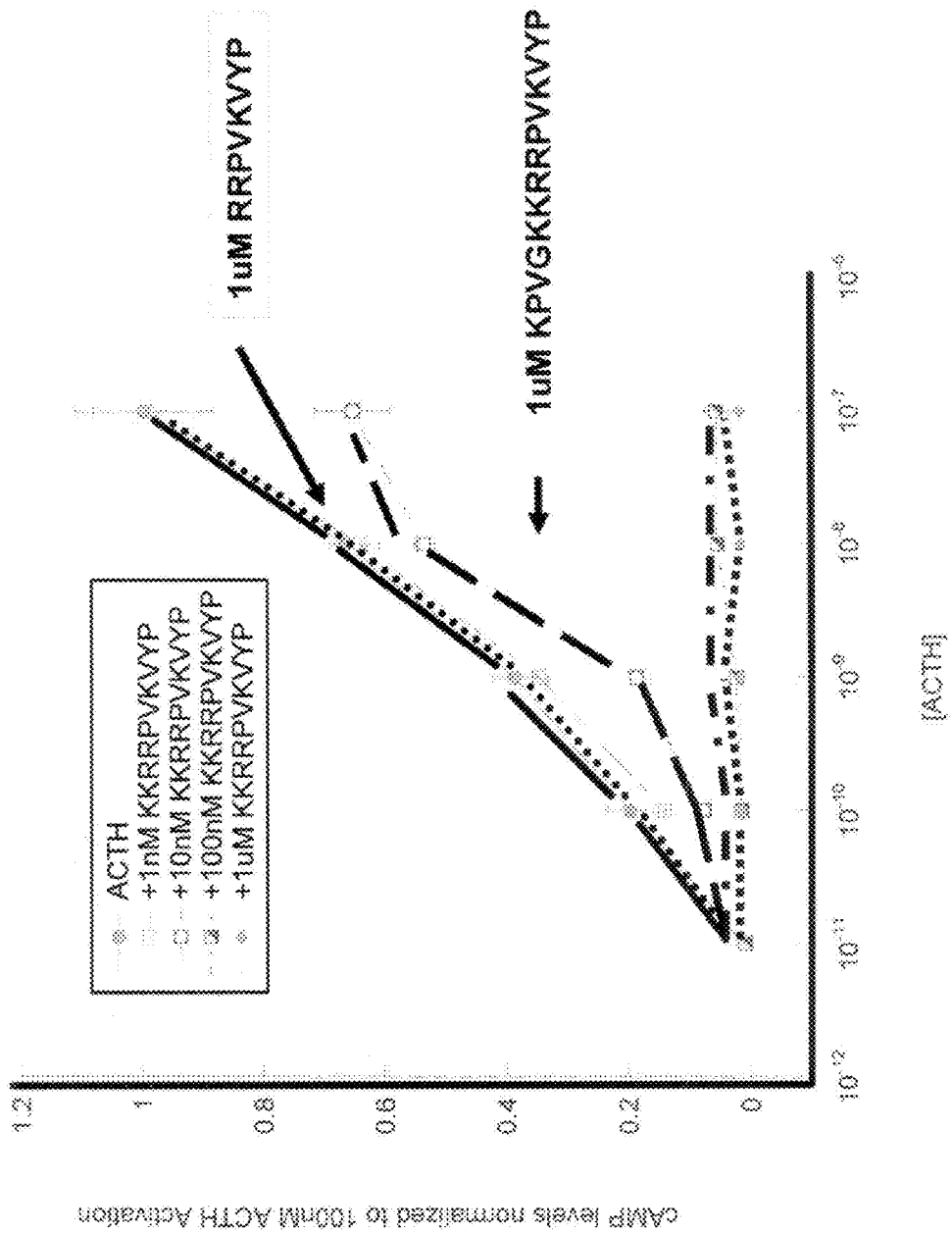
FIG. 1. Inhibition of ACTH(1-24) by ACTH(15-24) peptide. For all experiments, Chinese Hamster Ovary (CHO) cells were transiently transfected with a human melanocortin receptor gene construct (MC2R for FIGS. 1-3) and a mouse MRAP1 gene, as described in the Examples section. Two days later, individual wells of transfected CHO cells ($10^5$ cells per well) were incubated with ACTH(1-24) at concentrations ranging from $10^{-6}$ to $10^{-12}$ M. For these experiments, each concentration of ACTH(1-24) was co-incubated with either no KKRRPVKVYP (SEQ ID NO:1) (filled circle), $10^{-6}$ M KKRRPVKVYP (SEQ ID NO:1) (filled diamond), $10^{-7}$ M KKRRPVKVYP (SEQ ID NO:1) (half-filled square), $10^{-8}$ M KKRRPVKVYP (SEQ ID NO:1) (circle in square), or $10^{-9}$ M KKRRPVKVYP (SEQ ID NO:1) (open square). After a 15 minute incubation, the amount of cAMP produced in each well of CHO cells was measured. Each data point is a minimum of n=3. Transfected CHO stimulated with ACTH(1-24) alone produced cAMP in a dose dependent manner. However, when ACTH(1-24) was co-incubated with $10^{-6}$ M or $10^{-7}$ M KKRRPVKVYP (SEQ ID NO:1), there was complete blockage of hMC2R activation. Co-incubation of ACTH(1-24) with KKRRPVKVYP (SEQ ID NO:1) at $10^{-8}$ M resulted in a 34±5% drop inactivation, whereas co-incubation with KKRRPVKVYP (SEQ ID NO:1) at $10^{-9}$ M had no effect. The ACTH analog ACTH(17-24) [RRPVKVYP; SEQ ID NO:6] at a concentration of $10^{-6}$ M was co-incubated with ACTH (1-24) but had no inhibitory effect. The ACTH analog ACTH (11-24) [KPVGKKRRPVKVYP; SEQ ID NO:7] at a concentration of $10^{-6}$ M produced a 50% inhibition of ACTH(1-24) stimulation, but had no effect on ACTH(1-24) stimulation when tested at a concentration of $10^{-7}$ M.

The present invention relates to polypeptide analogs of adrenocorticotropin. hormone (ACTH) that comprise a KKRRP (SEQ ID N0:5) motif, a secondary site involved with melanocortin 2 receptor (MC2R) activation. The ACTH polypeptide analogs described herein find use in inhibiting ACTH-dependent activation of MC2R. Surprisingly, the inventors have found that the ACTH antagonist polypeptides described herein are more potent inhibitors of ACTH-dependent activation of MC2R than other ACTH antagonist analogs that have been previously described (see, e.g., WO 2006/052468 and U.S. Pat. No. 7,264,314). The ACTH antagonist polypeptides of the present invention are able to inhibit ACTH-dependent activation of MC2R at a concentration of $10^{-7}$ M, in contrast to previously described ACTH analogs, which are ineffective at $10^{-7}$ M.

ACTH-dependent activation of MC2R plays an important role in regulating and maintaining adrenocortical function. Aberrant activation of the ACTH-dependent MC2R signaling pathway is implicated in overproduction of glucocorticoids (when ACTH is overexpressed) or underproduction of glucocorticoids (when ACTH is underexpressed). Moreover, altered ACTH-dependent activation of MC2R (and thus, altered production of glucocorticoids) is associated with various diseases and biological conditions in, humans and non-human animals. For example, conditions such as Cushing's Syndrome, tumor of the anterior pituitary, chronic stress, and trauma are associated with the overproduction of the glucocorticoid cortisol. Therefore, antagonists of ACTH-dependent activation of MC2R can be useful in reducing cortisol production and treating diseases and conditions associated with cortisol overproduction.

Thus, in one aspect the present invention provides for methods of treating overproduction of cortisol in a subject and/or treating a subject having a condition characterized by overproduction of cortisol. In some embodiments, the methods comprise administering an agent that significantly inhibits ACTH-dependent activation of MC2R, e.g., an ACTH antagonist polypeptide as described herein. In another aspect, the present invention provides ACTH antagonist polypeptides as described herein as well as formulations and kits comprising the ACTH antagonist polypeptides as described herein.

II. ACTH Antagonist Polypeptides

It has been found that ACTH polypeptide analogs described herein function as a potent antagonist of ACTH(1-24). ACTH(1-24) comprises amino acid residues 1-24 of the human ACTH protein and has been shown to activate the melanocortin 2 receptor (MC2R) as fully as full-length human ACTH, activating signaling pathways downstream of MC2R and resulting in the production of cortisol. See Schwyzer, R.; 1977; ACTH: a short introductory review; $Ann. N.Y. Acad. Sci.$ 297:3-26. Therefore, an agent that is able to function as an antagonist of ACTH(1-24) will also likely function as an antagonist of full-length ACTH. As used herein, the numbering of the residues is in accordance with what is understood in the art and is with reference to SEQ ID NO:3 or GenBank Accession No. 720112A.

As described herein, ACTH polypeptide analogs comprising the amino acid sequence KKRRPVKVYP (SEQ ID NO:1) block activation of the MC2R receptor by ACTH. In particular, it has been found that ACTH polypeptide analogs comprising the amino acid sequence KKRRPVKVYP (SEQ ID NO:1) and at a concentration of 1 µM ($10^{-6}$ M) or 100 nM ($10^{-7}$ M) completely or nearly completely inhibit ACTH-dependent activation of MC2R at a range of ACTH concentrations from $10^{-6}$ to $10^{-12}$ M. Furthermore, ACTH polypeptide analogs comprising the amino acid sequence KKRRPVKVYP (SEQ ID NO:1) and at a concentration of 10 nM ($10^{-8}$ M) result in about a 34% decrease in ACTH-dependent activation of MC2R at a range of ACTH concentrations from $10^{-6}$ to $10^{-12}$ M. In contrast, previously described ACTH inhibitors (e.g., analogs described in WO 2006/052468 or in Seelig et al., $Methods in Enzymol.$ 39:347-59 (1975)) have at least some effectiveness in inhibiting ACTH when present at a concentration of $10^{-6}$ M, but are ineffective at lower concentrations such as $10^{-7}$ or $10^{-8}$ M. Thus, the ACTH antagonist polypeptides of the present invention are surprisingly more effective at inhibiting ACTH-dependent activation of MC2R, even at low concentrations.

Figure 2:
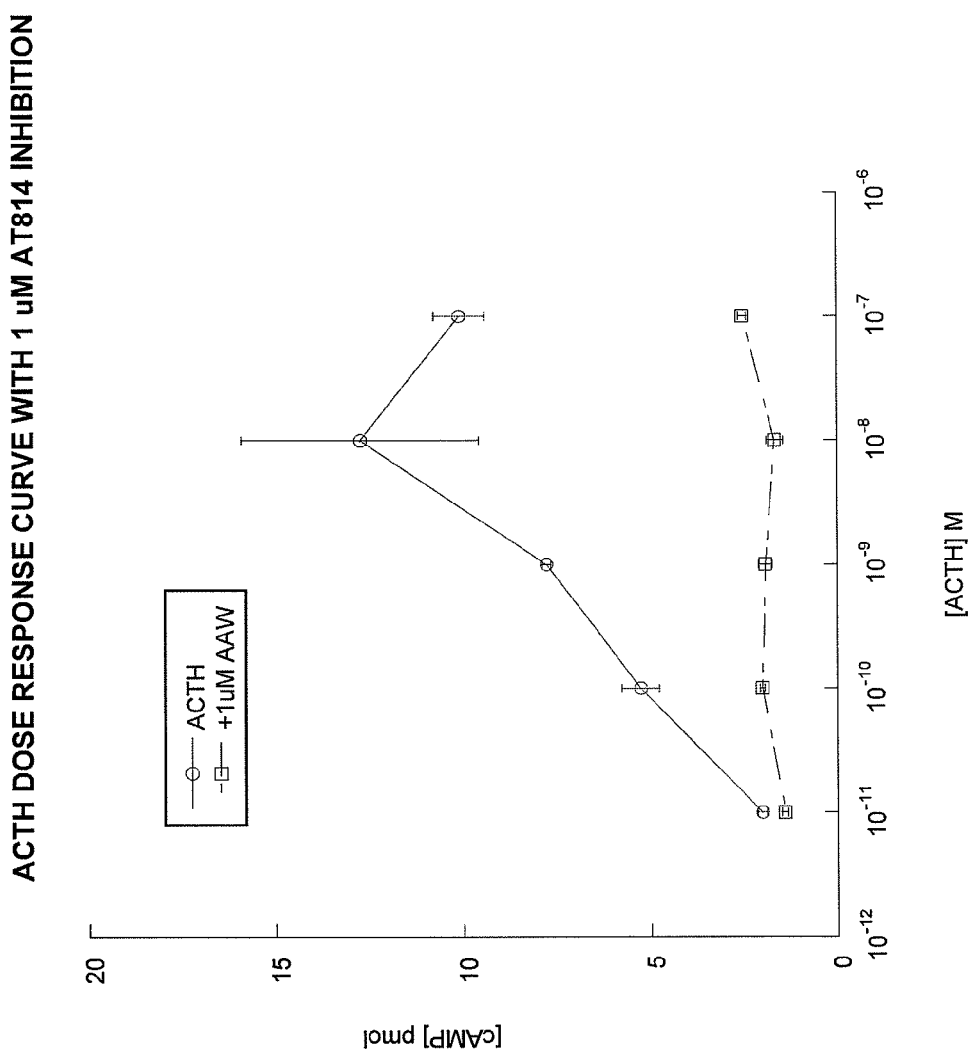
FIG. 2. Dose response curve for ACTH analog AT814. AT814 is a previously-described ACTH inhibitor (WO 2006/052468). For this experiment, individual wells of transfected CHO cells (as described for FIG. 1) were incubated with ACTH(1-24) at concentrations ranging from $10^{-6}$ to $10^{-12}$ M alone (open circle) or ACTH(1-24) and AT814 at a concentration of $10^{-6}$ M (open square). At $10^{-6}$ M, AT814 completely inhibited MC2R activation.

Additionally, the ACTH polypeptide analogs comprising the amino acid sequence KKRRPVKVYP (SEQ ID NO:1) are specific for regulating MC2R activation. Without being bound to a particular theory, it is believed that melanocortin receptors MC1R, MC3R, MC4R, and MC5R can be activated by ACTH or other melanocortin peptides and only require the HFRW (SEQ ID NO:8) motif for activation of the receptor; the KKRRP (SEQ ID NO:5) motif that is present at residues 15-19 of ACTH is not involved in activation of any of these non-MC2R melanocortin receptors. Because the ACTH polypeptide analogs comprising the amino acid sequence KKRRPVKVYP (SEQ ID NO:1) as described herein do not comprise a HFRW (SEQ ID NO:8) motif, they do not activate non-MC2R melanocortin receptors, in contrast to other previously described ACTH analogs such as those described in WO 2006/052468, as shown in FIG. 2. For instance, the ACTH analog AT814 described in WO 2006/052468 has the following sequence: SYSMEHFRWGK-PVGKRAAWVKVYP (SEQ ID NO:19). Thus, the ACTH antagonist polypeptides of the present invention (e.g., ACTH antagonist polypeptides having the amino acid sequence KKRRPVKVYP (SEQ ID NO:1) or KKRRPVKVYPN (SEQ ID NO:2)) are also advantageous over previously described ACTH analogs because they specifically inhibit ACTH-dependent MC2R activation without disrupting activation of non-MC2R melanocortin receptors.

Thus, in one aspect, the present invention provides polypeptide analogs of adrenocorticotropin hormone (ACTH) that reduce or eliminate ACTH-induced production of cortisol. In some embodiments, the ACTH polypeptide analogs antagonize ACTH by significantly inhibiting ACTH-dependent activation of MC2R, a melanocortin receptor that is specifically activated by ACTH but not by other peptide hormones, but that does not significantly inhibit activation of melanocortin receptors other than MC2R (i.e., MC1R, MC3R, MC4R, or MC5R). In some embodiments, the ACTH antagonist polypeptides comprise a truncated sequence of ACTH that includes the KKRRPVKVYP (SEQ ID NO:1) motif of ACTH (residues 15-24 of the human ACTH protein). In some embodiments, the ACTH antagonist polypeptide consists of the amino acid sequence KKRRPVKVYP (SEQ ID NO:1). In some embodiments, the ACTH antagonist polypeptide consists of the amino acid sequence KKRRPVKVYPN (SEQ ID NO:2).

A. Generation of ACTH Antagonist Polypeptides

The ACTH antagonist polypeptides of the present invention can be synthesized chemically using conventional peptide synthesis or other protocols well known in the art, by recombinant expression, or can be obtained from natural sources.

Peptides may be synthesized by solid-phase peptide synthesis methods using procedures similar to those described by Merrifield et al., $J. Am. Chem. Soc.,$ 85:2149-2156 (1963); Barany and Merrifield, $Solid-Phase Peptide Synthesis, in The Peptides: Analysis, Synthesis, Biology$ Gross and Meienhofer (eds.), Academic Press, N.Y., vol. 2, pp. 3-284 (1980); and Stewart et al., $Solid Phase Peptide Synthesis$ 2nd ed., Pierce Chem. Co., Rockford, Ill. (1984). During synthesis, N-α-protected amino acids having protected side chains are added stepwise to a growing polypeptide chain linked by its C-terminal and to a solid support, i.e., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc, which is acid labile, and Fmoc, which is base labile.

Materials suitable for use as the solid support are well known to those of skill in the art and include, but are not limited to, the following: halomethyl resins, such as chloromethyl resin or bromomethyl resin; hydroxymethyl resins; phenol resins, such as 4-(α-[2,4-dimethoxyphenyl]-Fmoc-aminomethyl) phenoxy resin; tert-alkyloxycarbonyl-hydrazidated resins, and the like. Such resins are commercially available and their methods of preparation are known by those of ordinary skill in the art.

Briefly, the C-terminal N-α-protected amino acid is first attached to the solid support. The N-α-protecting group is then removed. The deprotected a-amino group is coupled to the activated α-carboxylate group of the next N-α-protected amino acid. The process is repeated until the desired peptide is synthesized. The resulting peptides are then cleaved from the insoluble polymer support and the amino acid side chains deprotected. Longer peptides can be derived by condensation of protected peptide fragments. Details of appropriate chemistries, resins, protecting groups, protected amino acids and reagents are well known in the art and so are not discussed in detail herein (See, e.g., Atherton et al., *Solid Phase Peptide Synthesis: A Practical Approach*, IRL Press (1989), and Bodanszky, *Peptide Chemistry, A Practical Textbook,* 2nd Ed., Springer-Verlag (1993)).

Polypeptides can also be produced by recombinant expression. Basic texts disclosing general methods and techniques in the field of recombinant genetics include Sambrook and Russell, *Molecular Cloning, A Laboratory Manual* (3rd ed. 2001); Kriegler, *Gene Transfer and Expression: A Laboratory Manual* (1990); and Ausubel et al., eds., *Current Protocols in Molecular Biology* (1994). Recombinant expression can be in bacteria, such as *E. coli,* yeast, insect cells or mammalian cells.

B. Measuring Inhibition by ACTH Antagonist Polypeptides

Inhibition, reduction, or decrease in ACTH activity (e.g., ACTH-mediated activation of MC2R) by the ACTH antagonist polypeptides of the present invention can be measured by any method known in the art. In some embodiments, inhibition of ACTH activity is measured using an assay that measures MC2R downstream signaling, including but not limited to a cyclic AMP (cAMP) immunoassay. In some embodiments, inhibition of ACTH activity is measured by measuring the amount of secreted cortisol in a sample using an immunoassay.

A variety of immunoassay techniques can be used to detect the presence or level of MC2R downstream signaling molecules (e.g., cAMP) or cortisol. The term immunoassay encompasses techniques including, without limitation, enzyme immunoassays (EIA) such as enzyme multiplied immunoassay technique (EMIT), enzyme-linked immunosorbent assay (ELISA), antigen capture ELISA, sandwich ELISA, IgM antibody capture ELISA (MAC ELISA), and microparticle enzyme immunoassay (MEIA); capillary electrophoresis immunoassays (CEIA); radioimmunoassays (RIA); immunoradiometric assays (IRMA); fluorescence polarization immunoassays (FPIA); and chemiluminescence assays (CL). If desired, such immunoassays can be automated. Immunoassays can also be used in conjunction with laser induced fluorescence (see, e.g., Schmalzing and Nashabeh, *Electrophoresis,* 18:2184-2193 (1997); Bao, *J. Chromatogr. B. Biomed. Sci.,* 699:463-480 (1997)). Liposome immunoassays, such as flow-injection liposome immunoassays and liposome immunosensors, are also suitable for use in the present invention (see, e.g., Rongen et al., *J. Immunol. Methods,* 204:105-133 (1997)). In addition, nephelometry assays, in which the formation of protein/antibody complexes results in increased light scatter that is converted to a peak rate signal as a function of the marker concentration, are suitable for use in the present invention. Nephelometry assays are commercially available from Beckman Coulter (Brea, CA; Kit #449430) and can be performed using a Behring Nephelometer Analyzer (Fink et al., *J. Clin. Chem. Clin. Biol. Chem.,* 27:261-276 (1989)).

Antigen capture ELISA can be useful for determining the presence or level of MC2R downstream signaling molecules or cortisol in a sample. For example, in an antigen capture ELISA, an antibody directed to an analyte of interest is bound to a solid phase and sample is added such that the analyte is bound by the antibody. After unbound proteins are removed by washing, the amount of bound analyte can be quantitated using, e.g., a radioimmunoassay (see, e.g., Harlow and Lane, Antibodies: A Laboratory Manual, Cold Spring Harbor Laboratory, New York, 1988)). Sandwich ELISA can also be suitable for use in the present invention. For example, in a two-antibody sandwich assay, a first antibody is bound to a solid support, and the analyte of interest is allowed to bind to the first antibody. The amount of the analyte is quantitated by measuring the amount of a second antibody that binds the analyte. The antibodies can be immobilized onto a variety of solid supports, such as magnetic or chromatographic matrix particles, the surface of an assay plate (e.g., microtiter wells), pieces of a solid substrate material or membrane (e.g., plastic, nylon, paper), and the like. An assay strip can be prepared by coating the antibody or a plurality of antibodies in an array on a solid support. This strip can then be dipped into the test sample and processed quickly through washes and detection steps to generate a measurable signal, such as a colored spot.

A radioimmunoassay using, for example, an iodine-125 ($^{125}$I) labeled secondary antibody (Harlow and Lane, supra) is also suitable for determining the presence or level of MC2R downstream signaling molecules or cortisol in a sample. A secondary antibody labeled with a chemiluminescent marker can also be suitable for use in the present invention. A chemiluminescence assay using a chemiluminescent secondary antibody is suitable for sensitive, non-radioactive detection of marker levels. Such secondary antibodies can be obtained commercially from various sources, e.g., Amersham Lifesciences, Inc. (Arlington Heights, Ill.).

Specific immunological binding of an antibody to a MC2R downstream signaling molecule (e.g., cAMP) or cortisol can be detected directly or indirectly. Direct labels include fluorescent or luminescent tags, metals, dyes, radionuclides, and the like, attached to the antibody. An antibody labeled with iodine-125 ($^{125}$I) can be used for determining the levels of one or more analytes in a sample. A chemiluminescence assay using a chemiluminescent antibody specific for the analyte is suitable for sensitive, non-radioactive detection of marker levels. An antibody labeled with fluorochrome is also suitable for determining the levels of one or more analytes in a sample. Examples of fluorochromes include, without limitation, DAPI, fluorescein, Hoechst 33258, R-phycocyanin, B-phycoerythrin, R-phycoerythrin, rhodamine, Texas red, and lissamine. Secondary antibodies linked to fluorochromes can be obtained commercially, e.g., goat F(ab')$_2$ anti-human IgG-FITC is available from Tago Immunologicals (Burlingame, Calif.).

Indirect labels include various enzymes well-known in the art, such as horseradish peroxidase (HRP), alkaline phosphatase (AP), β-galactosidase, urease, and the like. A horseradish-peroxidase detection system can be used, for example, with the chromogenic substrate tetramethylbenzidine (TMB), which yields a soluble product in the presence of hydrogen peroxide that is detectable at 450 nm. An alkaline phosphatase detection system can be used with the chromogenic substrate p-nitrophenyl phosphate, for example, which yields a soluble product readily detectable at 405 nm. Similarly, a β-galactosidase detection system can be used with the chromogenic substrate o-nitrophenyl-β-D-galactopyranoside (ONPG), which yields a soluble product detectable at 410 nm. An urease detection system can be used with a substrate such as urea-bromocresol purple (Sigma Immunochemicals; St. Louis, Mo.). A useful secondary antibody linked to an enzyme can be obtained from a number of commercial sources, e.g., goat F(ab')$_2$ anti-human IgG-alkaline phosphatase can be purchased from Jackson ImmunoResearch (West Grove, Pa.).

A signal from the direct or indirect label can be analyzed, for example, using a spectrophotometer to detect color from a chromogenic substrate; a radiation counter to detect radiation such as a gamma counter for detection of $^{125}$I; or a fluorometer to detect fluorescence in the presence of light of a certain wavelength. For detection of enzyme-linked antibodies, a quantitative analysis of the amount of marker levels can be made using a spectrophotometer such as an EMAX Microplate Reader (Molecular Devices; Menlo Park, Calif.) in accordance with the manufacturer's instructions. If desired, the assays of the present invention can be automated or performed robotically, and the signal from multiple samples can be detected simultaneously.

As a non-limiting example, an immunoassay can be used to detect the presence and/or quantity of cAMP in a sample from a subject that has been treated with an ACTH antagonist polypeptide (e.g., a sample taken from a subject subsequent to administration of an ACTH antagonist polypeptide). The level of cAMP in the sample from the subject treated with the ACTH antagonist polypeptide can then be compared against a control sample (e.g., a sample taken from the subject prior to administration of the ACTH antagonist polypeptide) and the differences quantified. In some embodiments, an ACTH antagonist polypeptide is said to inhibit ACTH activity if the level of cAMP in the sample from the subject treated with the ACTH antagonist polypeptide is decreased by at least about 10%, at least about 20%, at least about 30%, at least about 40%, at least about 50%, at least about 60%, at least about 70%, at least about 80%, at least about 90% or more as compared to the control sample. Immunoassays for detecting cAMP in a sample are known in the art and readily commercially available (e.g., cAMP Immunoassay, R&D Systems (Minneapolis, Minn.); cAMP EIA Kit, Assay Designs (Ann Arbor, Mich.); and cAMP Direct Immunoassay Kit, Abcam (Cambridge, Mass.)).

As another non-limiting example, an immunoassay can be used to detect the presence and/or amount of cortisol in a sample from a subject that has been treated with an ACTH antagonist polypeptide (e.g., a sample taken from a subject subsequent to administration of an ACTH antagonist polypeptide). The level of cortisol in the sample from the subject treated with the ACTH antagonist polypeptide can then be compared against a control sample (e.g., a sample taken from the subject prior to administration of the ACTH antagonist polypeptide) and the differences quantified. In some embodiments, an ACTH antagonist polypeptide is said to inhibit ACTH activity if the level of cortisol in the sample from the subject treated with the ACTH antagonist polypeptide is decreased by at least about 10%, at least about 20%, at least about 30%, at least about 40%, at least about 50%, at least about 60%, at least about 70%, at least about 80%, at least about 90% or more as compared to the control sample. Immunoassays for detecting cortisol in a sample are known in the art and readily commercially available (e.g., HitHunter™ Cortisol Plus Assay Kit, DiscoveRx (Fremont, Calif.); Cortisol Immunoassay, R&D Systems (Minneapolis, Minn.); and DetectX® Cortisol Enzyme Immunoassay Kit, Arbor Assays (Ann Arbor, Mich.)).

III. Methods Using the ACTH Antagonist Polypeptides

In one aspect, the present invention provides methods of treating overproduction of cortisol or conditions characterized by the overproduction of cortisol in a human or non-human subject. In some embodiments, the method comprises administering to the subject an agent that significantly inhibits activation of a melanocortin 2 receptor (MC2R) without significantly inhibiting activation of a melanocortin receptor other than MC2R. In some embodiments, the agent is an ACTH antagonist polypeptide having the amino acid sequence of KKRRPVKVYP (SEQ ID NO:1). In some embodiments, the agent is an ACTH antagonist polypeptide having the amino acid sequence of KKRRPVKVYPN (SEQ ID NO:2). In some embodiments, the level of cortisol in the human or non-human subject is increased by at least about 10%, at least about 20%, at least about 30%, at least about 40%, at least about 50%, at least about 60%, at least about 70%, at least about 80%, at least about 90%, or more as compared to a control subject (e.g., a subject not having that disease or condition). In some embodiments, the subject is administered the agent (e.g., an ACTH antagonist polypeptide having agent having the amino acid sequence of KKRRPVKVYP (SEQ ID NO:1) or KKRRPVKVYPN (SEQ ID NO:2)) at a concentration of agent that is sufficient to inhibit ACTH-dependent activation of the MC2R by at least about 10%, at least about 20%, at least about 30%, at least about 40%, at least about 50%, at least about 60%, at least about 70%, at least about 80%, at least about 90% or more as compared to the level of ACTH-dependent activation of the MC2R in the absence of the agent.

In another aspect, the present invention provides methods of inhibiting ACTH-dependent activation of a MC2R receptor. In some embodiments, the method comprises contacting a cell expressing ACTH with an agent that significantly inhibits activation of a melanocortin 2 receptor (MC2R) without significantly inhibiting activation of a melanocortin receptor other than MC2R. In some embodiments, the agent is an ACTH antagonist polypeptide having the amino acid sequence of KKRRPVKVYP (SEQ ID NO:1). In some embodiments, the agent is an ACTH antagonist polypeptide having the amino acid sequence of KKRRPVKVYPN (SEQ ID NO:2). In some embodiments, the cell is contacted with the agent (e.g., an ACTH antagonist polypeptide having agent having the amino acid sequence of KKRRPVKVYP (SEQ ID NO:1) or KKRRPVKVYPN (SEQ ID NO:2)) at a concentration of agent that is sufficient to inhibit ACTH-dependent activation of the MC2R by at least about 10%, at least about 20%, at least about 30%, at least about 40%, at least about 50%, at least about 60%, at least about 70%, at least about 80%, at least about 90% or more as compared to the level of ACTH-dependent activation of the MC2R in the absence of the agent. In some embodiments, the cell is an adrenocortical cell.

Conditions Characterized by Overproduction of Cortisol

In some embodiments, the agents of the present invention (e.g., the ACTH antagonist polypeptides as described herein) find use in the treatment of human and non-human subjects having conditions characterized by the overproduction of cortisol. Exemplary conditions include, but are not limited to, Cushing's Syndrome, tumor of the anterior pituitary, chronic stress, trauma, impaired immune response as a result of hypersecretion of cortisol, and initiation of premature labor.

With respect to therapeutic uses, the agents of the present invention (e.g., the ACTH antagonist polypeptides as described herein) can be administered to a subject in need thereof in a therapeutically effective amount. For example, an ACTH antagonist polypeptide (e.g., a polypeptide having the amino acid sequence of KKRRPVKVYP (SEQ ID NO:1) or KKRRPVKVYPN (SEQ ID NO:2)) can be administered in an amount sufficient to reduce the amount of ACTH-induced cortisol that is produced and/or secreted by at least about 10%, at least about 20%, at least about 30%, at least about 40%, at least about 50%, at least about 60%, at least about 70%, at least about 80%, at least about 90%, or more, wherein the level of cortisol production and/or secretion is measured by any method known in the art.

In some embodiments, treatment of a condition characterized by overproduction of cortisol is carried out by administering a therapeutically effective amount of an agent as described herein (e.g., an ACTH antagonist polypeptide having the amino acid sequence of KKRRPVKVYP (SEQ ID NO:1) or KKRRPVKVYPN (SEQ ID NO:2)). In some embodiments, a therapeutically effective amount is an amount sufficient to inhibit activation of MC2R by ACTH by at least 10%, at least 20%, at least 30%, at least 40%, at least 50%, at least 60%, at least 70%, at least 80%, at least 90% or more as compared to the amount of activation of MC2R by ACTH prior to administration of the agent. The activation of MC2R can be measured according to any method known in the art, including but not limited to measuring cAMP production or cortisol secretion as described above.

Aquaculture and Animal Husbandry

In some embodiments, the agents of the present invention (e.g., the ACTH antagonist polypeptides as described herein) find use in treating non-human animals, for example, animals being raised in fisheries, hatcheries, or other enclosed quarters for agricultural or aquacultural purposes. In some situations, the population density of animals raised in enclosed quarters for commercial agriculture and aquaculture is high enough that it induces stress in the animals. In response to stress, the pituitary gland (or its equivalent, for example the hypothalamo-pituitary-interrenal axis in fish) stimulates the production of ACTH, which in turn increases production of cortisol in the animals. Chronic stress in animals due to overcrowding can result in reduced production efficiency, reduced growth and meat yields, and lower immune system function.

Thus, in some embodiments, the methods of the present invention can be used for reducing cortisol production in fish (e.g., salmon, tilapia, carp, cod, seabass, and catfish), fowl (e.g., chickens, ducks, turkeys, and game birds), and livestock (e.g., cows, sheep, pigs, and goats). In some embodiments, prior to treatment with an agent of the present invention, the animal produces cortisol at a level that is associated with chronic stress in the animal.

In some embodiments, the method comprises administering an ACTH antagonist polypeptide (e.g., a polypeptide having the amino acid sequence of KKRRPVKVYP (SEQ ID NO:1) or KKRRPVKVYPN (SEQ ID NO:2)) at a concentration sufficient to reduce the level of cortisol production and/or secretion by at least about 10%, at least about 20%, at least about 30%, at least about 40%, at least about 50%, at least about 60%, at least about 70%, at least about 80%, at least about 90%, or more, wherein the level of cortisol production and/or secretion is measured by any method known in the art. In some embodiments, the agent is administered by injecting or implanting the ACTH antagonist polypeptide into the animal. In some embodiments, the agent is administered in a sustained release formulation.

IV. Formulations and Administration

In another aspect, the present invention provides pharmaceutical compositions comprising an agent that significantly inhibits activation of a melanocortin 2 receptor (MC2R) without significantly inhibiting activation of a melanocortin receptor other than MC2R. In some embodiments, the pharmaceutical composition comprises an ACTH antagonist polypeptide having the amino acid sequence of KKRRPVKVYP (SEQ ID NO:1). In some embodiments, the pharmaceutical composition comprises an ACTH antagonist polypeptide having the amino acid sequence of KKRRPVKVYPN (SEQ ID NO:2). In some embodiments, the pharmaceutical composition further comprises one or more additional therapeutic agents, including but not limited to chemotherapeutic agents, anti-inflammatory agents, or cortisol-inhibiting drugs (e.g., ketoconazole, mitotane, aminoglutethimide, or metyrapone).

In some embodiments, a pharmaceutical composition comprising an agent that significantly inhibits activation of a melanocortin 2 receptor (MC2R) without significantly inhibiting activation of a melanocortin receptor other than MC2R (e.g., a polypeptide having the amino acid sequence of KKRRPVKVYP (SEQ ID NO:1) or KKRRPVKVYPN (SEQ ID NO:2)) further comprises one or more additional pharmaceutically acceptable components. See, Remington: The Science and Practice of Pharmacy, 21$^{st}$ Ed., 2005, University of the Sciences in Philadelphia (USIP). For example, a pharmaceutical composition can also include, depending on the formulation desired, pharmaceutically-acceptable, non-toxic carriers, excipients, or diluents, which are defined as vehicles commonly used to formulate pharmaceutical compositions for animal or human administration. The diluent is selected so as not to affect the biological activity of the combination. Examples of such diluents are distilled water, physiological phosphate-buffered saline, Ringer's solutions, dextrose solution, and Hank's solution. In addition, the pharmaceutical composition or formulation may also include other carriers, adjuvants, or nontoxic, nontherapeutic, nonimmunogenic stabilizers and the like. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like.

The concentration of active agent in these formulations can vary widely, and will be selected primarily based on fluid volumes, viscosities, body weight and the like in accordance with the particular mode of administration selected and the subject's needs. Typically, a therapeutically effective dose or efficacious dose of the agent (e.g., a polypeptide having the amino acid sequence of KKRRPVKVYP (SEQ ID NO:1) or KKRRPVKVYPN (SEQ ID NO:2)) is employed in the pharmaceutical compositions of the invention. In some embodiments, the therapeutically effective dose or efficacious dose of the agent is about 0.001 mg/kg to about 1000 mg/kg daily. For example, a daily dose range of about 0.01 mg/kg to about 500 mg/kg, or about 0.1 mg/kg to about 200 mg/kg, or about 1 mg/kg to about 100 mg/kg, or about 10 mg/kg to about 50 mg/kg, can be used. The agents are formulated into pharmaceutically acceptable dosage forms by conventional methods known to those of skill in the art. Dosage regimens are adjusted to provide the desired response (e.g., a therapeutic response). In determining a therapeutically or prophylactically effective dose, a low dose can be administered and then incrementally increased until a desired response is achieved with minimal or no undesired side effects. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Actual dosage levels of the active ingredients in the pharmaceutical compositions of the present invention can be varied so as to obtain an amount of the active ingredient which is effective to achieve the desired therapeutic response for a particular patient, composition, and mode of administration, without being toxic to the patient. The selected dosage level depends upon a variety of pharmacokinetic factors including the activity of the particular compositions of the present invention employed, or the ester, salt or amide thereof, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors.

A pharmaceutical composition comprising an agent that significantly inhibits activation of a melanocortin 2 receptor (MC2R) without significantly inhibiting activation of a melanocortin receptor other than MC2R (e.g., a polypeptide having the amino acid sequence of KKRRPVKVYP (SEQ ID NO:1) or KKRRPVKVYPN (SEQ ID NO:2)) and optionally comprising a pharmaceutically acceptable excipient can be administered to a human subject or to a non-human subject, e.g., a non-human mammal (e.g., mouse), a bird (e.g., chicken), or a fish (e.g., salmon). Administration can be achieved in various ways, including oral, buccal, parenteral, including intravenous, intradermal, subcutaneous, intramuscular, transdermal, transmucosal, intranasal, etc., administration.

For oral administration, an agent of the present invention (e.g., a polypeptide having the amino acid sequence of KKRRPVKVYP (SEQ ID NO:1) or KKRRPVKVYPN (SEQ ID NO:2)) can be formulated readily by combining with pharmaceutically acceptable carriers that are well known in the art. Such carriers enable the compounds to be formulated as tablets, pills, dragees, capsules, emulsions, lipophilic and hydrophilic suspensions, liquids, gels, syrups, slurries, suspensions and the like, for oral ingestion by a patient to be treated. Pharmaceutical preparations for oral use can be obtained by mixing the compounds with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds can be dissolved or suspended in suitable liquids, such as fatty oils, liquid paraffin, or liquid polyethylene glycols. In addition, stabilizers can be added. All formulations for oral administration should be in dosages suitable for such administration.

Dragee cores are provided with suitable coatings. For this purpose, concentrated sugar solutions can be used, which can optionally contain gum arabic, talc, polyvinyl pyrrolidone, carbopol gel, polyethylene glycol, and/or titanium dioxide, lacquer solutions; and suitable organic solvents or solvent mixtures. Dyestuffs or pigments can be added to the tablets or dragee coatings for identification or to characterize different combinations of active compound doses.

An agent of the present invention (e.g., a polypeptide having the amino acid sequence of KKRRPVKVYP (SEQ ID NO:1) or KKRRPVKVYPN (SEQ ID NO:2)) can be formulated for parenteral administration, such as, for example, by intraarticular (in the joints), intravenous, intramuscular, intratumoral, intradermal, intraperitoneal, and subcutaneous routes. For parenteral administration, the agent can be formulated into a preparation by dissolving, suspending or emulsifying the agent in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. Preferably, an agent of the invention can be formulated in aqueous solutions, preferably in physiologically compatible buffers such as Hanks's solution, Ringer's solution, or physiological saline buffer. Formulations for injection can be presented in unit dosage form, e.g., in ampules or in multi-dose containers, with an added preservative. The compositions can take such, forms as suspensions, solutions or emulsions in oily or aqueous vehicles, and can contain formulatory agents such as suspending, stabilizing and/or dispersing agents.

For buccal administration, the compositions can take the form of tablets or lozenges formulated in a conventional manner.

In some embodiments, an agent of the present invention (e.g., a polypeptide having the amino acid sequence of KKRRPVKVYP (SEQ I1 NO:1) or KKRRPVKVYPN (SEQ ID NO:2)) is prepared for delivery in a sustained-release, controlled release, extended-release, timed-release or delayed-release formulation, for example, in semi-permeable matrices of solid hydrophobic polymers containing the therapeutic agent. Various types of sustained-release materials have been established and are well known by those skilled in the art. Current extended-release formulations include film-coated tablets, multiparticulate or pellet systems, matrix technologies using hydrophilic or lipophilic materials and wax-based tablets with pore-forming excipients (see, for example, Huang, et al. *Drug Dev. Ind. Pharm.* 29:79 (2003); Pearnchob, et al. *Drug Dev. Ind. Pharm.* 29:925 (2003); Maggi, et al. *Eur. J. Pharm. Biopharm.* 55:99 (2003); Khanvilkar, et al., *Drug Dev. Ind. Pharm.* 228:601 (2002); and Schmidt, et al., *Int. J. Pharm.* 216:9 (2001)). Sustained-release delivery systems can, depending on their design, release the agent over the course of hours or days, for instance, over 4, 6, 8, 10, 12, 16, 20, 24 hours or more. Usually, sustained release formulations can be prepared using naturally-occurring or synthetic polymers, for instance, polymeric vinyl pyrrolidones, such as polyvinyl pyrrolidone (PVP); carboxyvinyl hydrophilic polymers; hydrophobic and/or hydrophilic hydrocolloids, such as methylcellulose, ethylcellulose, hydroxypropylcellulose, and hydroxypropylmethylcellulose; and carboxypolymethylene.

Sustained-release or extended-release formulations can also be prepared using natural ingredients, such as minerals, including titanium dioxide, silicon dioxide, zinc oxide, and clay (see, U.S. Pat. No. 6,638,521, herein incorporated by reference). Exemplified extended release formulations that can be used in delivering an agent of the present invention (e.g., a polypeptide having the amino acid sequence of KKRRPVKVYP (SEQ ID NO:1) or KKRRPVKVYPN (SEQ ID NO:2)) include those described in U.S. Pat. Nos. 6,635,680; 6,624,200; 6,613,361; 6,613,358; 6,596,308; 6,589,563; 6,562,375; 6,548,084; 6,541,020; 6,537,579; 6,528,080; and 6,524,621, each of which is hereby incorporated herein by reference. Controlled release formulations of particular interest include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817; and 5,296,483, each of which is hereby incorporated herein by reference. Those skilled in the art will readily recognize other applicable sustained release formulations.

The pharmaceutical compositions also can comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

The agents described herein (e.g., a polypeptide having the amino acid sequence of KKRRPVKVYP (SEQ ID NO:1) or KKRRPVKVYPN (SEQ II) NO:2)) can also be administered in conjunction with another type of therapeutic treatment, including but not limited to tumor treatment (e.g., radiation, chemotherapy, surgical removal of a tumor, immunotherapy, or a combination of such treatments), treatment for ACTH hypersecretion (e.g., drug treatment or adrenalectomy), or other medical treatment.

V. Kits

In another aspect, the present invention provides for kits comprising an agent that significantly inhibits activation of a melanocortin 2 receptor (MC2R) without significantly inhibiting activation of a melanocortin receptor other than MC2R. In some embodiments, the kit comprises a polypeptide having the amino acid sequence of KKRRPVKVYP (SEQ ID NO:1). In some embodiments, the kit comprises a polypeptide having the amino acid sequence of KKRRPVKVYPN (SEQ ID NO:2). In some embodiments, the kit comprises a polypeptide having the amino acid sequence of KKRRPVKVYP (SEQ ID NO:1) or KKRRPVKVYPN (SEQ ID NO:2) and a pharmaceutically acceptable excipient.

Optionally, the kit can comprise an agent as described herein (e.g., a polypeptide having the amino acid sequence of KKRRPVKVYP (SEQ ID NO:1) or KKRRPVKVYPN (SEQ ID NO:2)) and one or more additional therapeutic agents, including but not limited to chemotherapeutic agents, anti-inflammatory agents, or cortisol-inhibiting drugs (e.g., ketoconazole, mitotane, aminoglutethimide, or metyrapone). In some embodiments, the kit comprises an agent as described herein and one or more additional therapeutic agents in separate formations. In some embodiments, the agent and the one or more additional therapeutic agents are within the same formation. In some embodiments, a kit provides an agent as described herein and one or more additional therapeutic agents independently in uniform dosage formulations throughout the course of treatment. In some embodiments, a kit provides an agent as described herein and one or more additional therapeutic agents independently in graduated dosages over the course of treatment, either increasing or decreasing, but usually increasing to an efficacious dosage level, according to the requirements of an individual.

EXAMPLES

The following examples are intended to illustrate, but not to limit, the claimed invention.

Example 1

Inhibition of MC2R Activation by ACTH(15-24)

The overproduction of ACTH(1-39) by the anterior pituitary gland, for example as a result of Cushing's Syndrome or due to chronic stress, leads to the overstimulation of melanocortin 2 receptors (MC2R) on adrenal cortical cells and the subsequence overproduction of cortisol. One strategy for disrupting this cascade is to block the activation of MC2R by introducing an ACTH antagonist. From previous studies, it was known that: (a) all melanocortin peptides activate melanocortin receptors via the HFRW (SEQ ID NO:8) motif present near the N-terminal of these peptides; (b) α-MSH (NAc-SYSMEHFRWGKPV-NH$_2$; SEQ ID NO:9) has the HFRW (SEQ ID NO:8) motif but cannot activate MC2R; and (c) ACTH(1-24) [SYSMEHFRWGKPVGKKRRPVKVYP; SEQ ID NO:4] is as potent an activator of MC2R as ACTH (1-39). Collectively, these data point to the KKRRPVKVYP (SEQ ID NO:1) region in ACTH as a second site involved in the activation of MC2R.

To test this hypothesis, a human MC2R gene construct was transiently co-transfected with a mouse MCR2R accessory protein 1 (MRAP1) gene into CHO cells and subsequently, cAMP production was measured.

MC2R and MRAP Constructs

Human hMC2R, Genbank Accession No. AY225229.1, was synthesized by GenScript with a V-5 epitope tag and inserted into a pcDNA3.1 vector. Mouse (*Mus musculus*) mMRAP1, Genbank Accession No. NM_029844, was also synthesized by GenScript with a FLAG epitope tag and inserted into pcDNA3.1 vectors.

Tissue Culture

The experiments were all done in transiently transfected CHO cells. The CHO cells were grown at 37° C. in a humidified 5% $CO_2$ incubator in Kaighn's Modification of Ham's F-12 (2 mM glutamine, 1500 mg/L bicarbonate) with 10% fetal bovine serum, 5 mL pen/strep, and 1 mL normocin.

Functional Expression of MC2R

In order to functionally express hMC2R in heterologous cells, like CHO cells, the hMC2R construct must be co-transfected with a mammalian MRAP (melanocortin receptor accessory protein; Hinkle, P. M. and Sebag, J. A. (2009) Structure and function of the melanocortin 2 receptor accessory protein. *Mol. Cell. Endocrinol.* 300:25-31). CHO cells were transfected with 2 μg of hMC2R and mMRAP using a Cell Line Nucleofector Kit (Amaxa, Inc.) with solution T and program U-023. The cells were then plated on a white, 96-well plate a density of $1 \times 10^5$ cells per well. 48 hours after transfection, cells were stimulated with the appropriate ligands in serum-free CHO media for 15 minutes at 37° C. at concentrations ranging from $10^{-5}$ M to $10^{-10}$ M. After a 15 minute incubation, a direct cAMP EIA kit (Assay Designs, Ann Arbor, Mich.) was used to measure cAMP in the CHO cells.

Data Analysis

All experimental treatments were performed in no less than triplicate, and then corrected for control values, which were obtained by using transfected cells that were left unstimulated. In each of the assays, maximal activation levels were between three to 10 times the control level. Corrected values were normalized to 100 nM ACTH activation. Average values and standard errors of the mean were graphed using Kaleida-Graph software, and the $K_4$ value for each ligand was determined.

TABLE 1

Activation of MC2R by ACTH analogs

| ACTH analog | SEQ ID NO: | MC2R activation relative to full-length ACTH |
|---|---|---|
| SYSMEHFRWGKPVGKKRRPVKVYP | 4 | Full activity |
| SYSMEAAAAGKPVGKKRRPVKVYP | 10 | No activity |
| SYSMEHFAWGKPVGKKRRPVKVYP | 11 | No activity |
| SYSMEHARWGKPVGKKRRPVKVYP | 12 | No activity |
| SYSMEHFRWGKPVGAAAAAVKVYP | 13 | No activity |
| SYSMEHFRWGKPVGAARRPVKVYP | 14 | 100 fold drop in activity |
| SYSMEHFRWGKPVGKKAAAVKVYP | 15 | 100 fold drop in activity |
| SYSMEHFRWAAAAAKKRRPVKVYP | 16 | 400 fold drop in activity |
| KKRRPVKVYP | 1 | No activity |
| RRPVKVYP | 6 | No activity |

While ACTH(1-24) produced a robust standard curve, the analog SYSMEHFRWGKPVGAAAAAVKVYP (SEQ ID NO:13) was 1000-fold less potent. Although these data indicated a role for the KKRRP (SEQ ID NO:5) motif in the activation of the receptor, the KKRRPVKVYP (SEQ ID NO:1) analog when incubated alone did not activate hMC2R. However, when concentrations of ACTH(1-24) ranging from $10^{-6}$ to $10^{-12}$ M were co-incubated with either $10^{-6}$ or $10^{-7}$ M KKRRPVKVYP (SEQ ID NO:1), there was complete blockage of hMC2R activation (FIG. 1). Co-incubation of ACTH (1-24) with KKRRPVKVYP (SEQ ID NO:1) at $10^{-8}$ M resulted in a 34±5% drop in activation. In contrast, the analog RRPVKVYP (SEQ ID NO:6) ($10^{-6}$ M) did not block the activation of hMC2R by ACTH(1-24) (FIG. 1). These results suggest the importance of residues K15 and K16 for the activation of hMC2R. In addition, the analog KKRRPAAAA (SEQ ID NO:17) ($10^{-6}$ M) did not block the activation of hMC2R by ACTH(1-24). These results suggest that residues in the VKVYP (SEQ ID NO:18) region may facilitate the binding of the KKRRPVKVYP (SEQ ID NO:1) analog to a site on hMC2R. In conclusion, the analog ACTH(15-24) can function as an ACTH(1-24) antagonist in our in vitro system, and may also be useful as an in vivo antagonist of ACTH activation of MC2R under conditions in which it would be desirable to lower the levels of circulating cortisol.

Example 2

Comparison of Dose Response Curves for ACTH(15-24) and ACTH Antagonist AT814

The MC2 receptor (ACTH receptor) on adrenal cells has two binding sites. One binding site accommodates the HFRW (SEQ ID NO:8) motif in ACTH(1-24) and the other binding site accommodates the KKRRP (SEQ ID NO:5) binding site [SYSMEHFRWGKPVGKKRRPVKVYP; SEQ ID NO:4]. We hypothesized that if the KKRRP (SEQ ID NO:5) site were occupied, then ACTH(1-24) would not be able to activate MC2R. As shown in FIG. 1, this hypothesis is correct. Co-incubation of ACTH(1-24) with the inhibitor ACTH(15-24) completely blocked activation of the receptor at concentrations of $10^{-6}$ M and $10^{-7}$ M, and resulted in partial blockage of activation at a concentration of $10^{-8}$ M.

Figure 3:
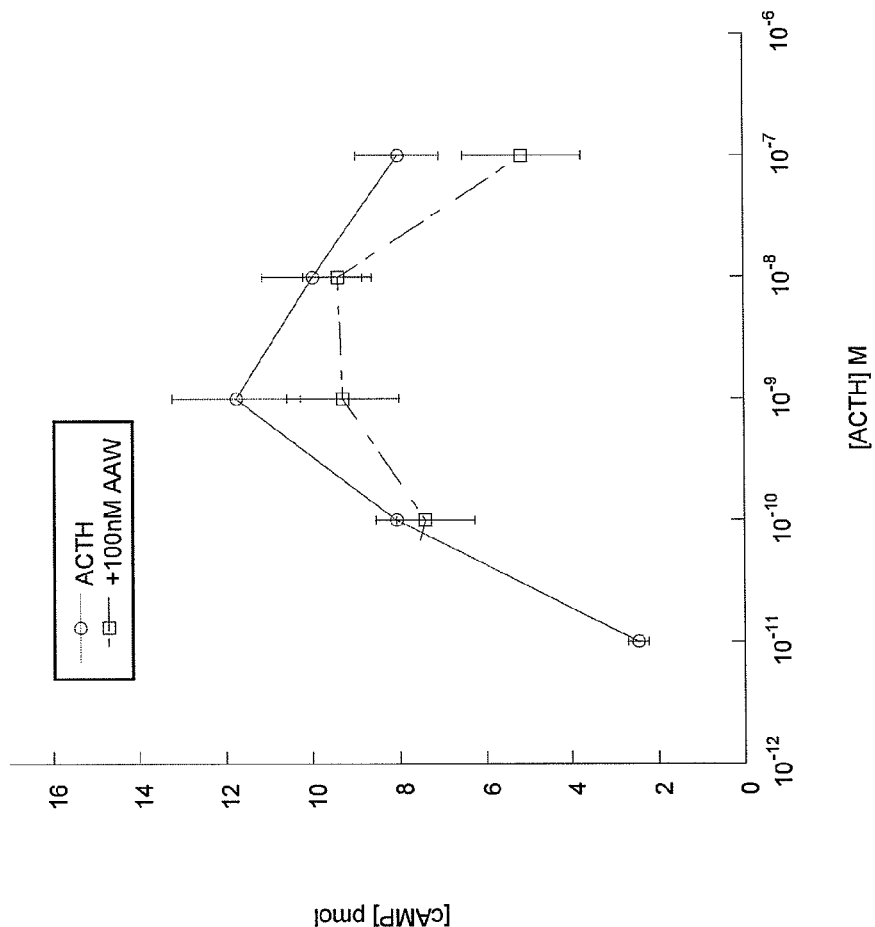
FIG. 3. Dose response curve for ACTH analog AT814. The experiment presented in FIG. 2 was repeated using AT814 at a concentration of $10^{-7}$ M. AT814 had no inhibitory effect at this concentration. Open circles: ACTH(1-24) alone; open squares: ACTH(1-24)+AT814 ($10^{-7}$ M).
Figure 4:
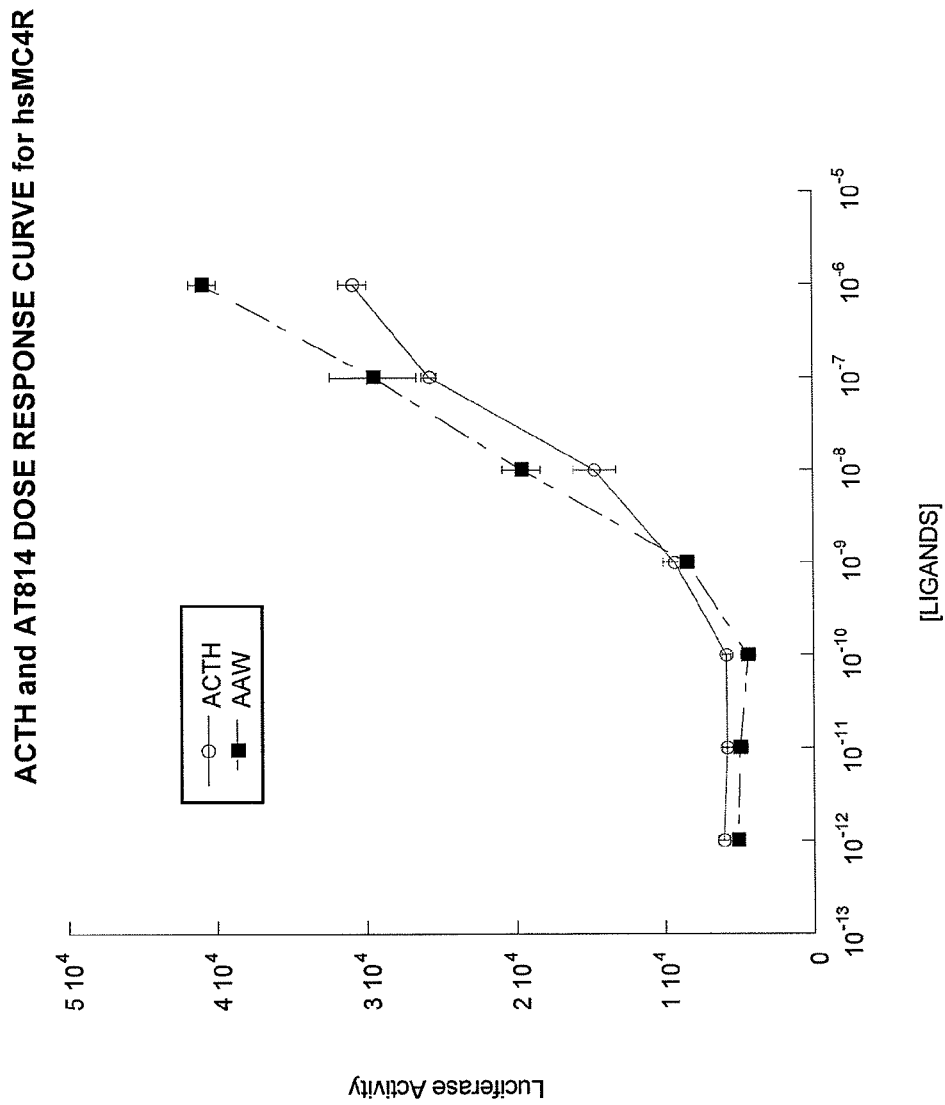
FIG. 4. Activation of human MC4R by ACTH analog AT814. Because AT814 has the HFRW (SEQ ID NO:8) motif, the hypothesis that this analog could activate the human MC4 receptor was tested. CHO cells were transfected with a human MC4R cDNA construct in a pcDNA3.1 vector. The hMC4R-transfected CHO cells were incubated with AT814 at concentrations ranging from $10^{-6}$ to $10^{-12}$ M, and the AT814 analog stimulated the production of cAMP in a dose dependent manner.

AT814 is another example of an analog designed to block the activation of the MC2 receptor. However, unlike ACTH (15-24), AT814 has some specific limitations. AT814 [SYSMEHFRWGKPVGKRAAWVKVYP; SEQ ID NO:19] has a modified KKRRP (SEQ ID NO:5) motif (underlined). This analog can act as a competitive inhibitor of ACTH(1-24) activation of MC2R at a concentration of $10^{-6}$ M (FIG. 2), but is ineffective at a concentration of $10^{-7}$ M (FIG. 3). Another drawback of AT814 is that this analog can activate the human MC4 receptor (FIG. 4). Because the hMC4 receptor, as well as the human MC1, MC3, and MC5 receptors can all be activated by ACTH(1-24) (Cone, R. D.; Studies on the physiological functions of the melanocortin system; *Endocrine Reviews* 27:736-749(2006)), AT814 may have unintended side effects if injected into subjects. In contrast, because the ACTH antagonist polypeptides of the present invention (e.g., ACTH(15-24)) lack the HFRW (SEQ ID NO:8) motif, these analogs cannot activate any melanocortin receptor other than MC2R.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A method of treating a subject having a condition characterized by overproduction of cortisol, the method comprising administering to the subject an agent that significantly inhibits activation of a melanocortin 2 receptor (MC2R) without significantly inhibiting activation of a melanocortin receptor other than MC2R, wherein the agent is a polypeptide consisting of the amino acid sequence of KKRRPVKVYP (SEQ ID NO:1) or KKRRPVKVYPN (SEQ ID NO:2).

2. The method of claim 1, wherein the agent is a polypeptide consisting of the amino acid sequence of SEQ ID NO:1.

3. The method of claim 1, wherein the agent is a polypeptide consisting of the amino acid sequence of SEQ ID NO:2.

4. The method of claim 1, wherein the agent reduces adrenocorticotropin hormone (ACTH)-induced production of cortisol by at least 10%.

5. The method of claim 1, wherein the subject is a human.

6. The method of claim 1, wherein the condition is selected from the group consisting of Cushing's syndrome, tumor of the anterior pituitary, chronic stress, and trauma.

7. The method of claim 6, wherein the condition is Cushing's syndrome.

8. The method of claim 1, wherein the agent is administered systemically.

9. The method of claim 1, wherein the agent is administered by intravenous injection.

10. The method of claim 1, wherein the agent is administered in a sustained release formulation.

11. A method of treating overproduction of cortisol in a population of non-human animals, the method comprising administering to the non-human animals an agent that significantly inhibits activation of a melanocortin 2 receptor (MC2R) without significantly inhibiting activation of a melanocortin receptor other than MC2R, wherein the agent is a polypeptide consisting of the amino acid sequence of KKRRPVKVYP (SEQ ID NO:1) or KKRRPVKVYPN (SEQ ID NO:2).

12. The method of claim 11, wherein the non-human animals produce cortisol at a level that is associated with chronic stress in the non-human animals.

13. The method of claim 11, wherein the agent is a polypeptide consisting of the amino acid sequence of SEQ ID NO:1.

14. The method of claim 11, wherein the agent is a polypeptide consisting of the amino acid sequence of SEQ ID NO:2.

15. The method of claim 11, wherein the agent reduces adrenocorticotropin hormone (ACTH)-induced production of cortisol by at least 10%.

16. The method of claim 11, wherein the non-human animals are fish.

17. The method of claim 11, wherein the non-human animals are chickens.

18. The method of claim 11, wherein the agent is administered in a sustained release formulation.

19. A method of inhibiting adrenocorticotropin hormone (ACTH)-dependent activation of a melanocortin 2 receptor (MC2R), the method comprising contacting a cell expressing ACTH with a polypeptide consisting of the amino acid sequence of KKRRPVKVYP (SEQ ID NO:1) or KKRRPVKVYPN (SEQ ID NO:2); thereby inhibiting ACTH-dependent activation of the MC2R.

20. The method of claim 19, wherein the cell is contacted with the polypeptide at a concentration sufficient to inhibit ACTH-dependent activation of the MC2R by at least 50%.

21. The method of claim 19, wherein the polypeptide consists of the amino acid sequence of SEQ ID NO:1.

22. The method of claim 19, wherein the polypeptide consists of the amino acid sequence of SEQ ID NO:2.

* * * * *